United States Patent [19]
Spitsberg et al.

[11] Patent Number: 5,635,401
[45] Date of Patent: Jun. 3, 1997

[54] METHOD TO DETECT HORMONE TREATMENT IN ANIMALS

[75] Inventors: Vitaly L. Spitsberg, Ithaca; Ronald C. Gorewit, Slaterville Springs, both of N.Y.

[73] Assignee: Cornell Research Foundation, Inc., Ithaca, N.Y.

[21] Appl. No.: 526,059

[22] Filed: Sep. 8, 1995

[51] Int. Cl.$^6$ .................................................. G01N 33/06
[52] U.S. Cl. ............................... 436/23; 436/20; 436/22; 436/86; 436/87; 424/535
[58] Field of Search .................................. 436/20, 22, 23, 436/86, 87; 424/535; 422/74

[56] References Cited

U.S. PATENT DOCUMENTS 5,004,728  4/1991  Chalupa et al. ...................... 514/12

OTHER PUBLICATIONS

Spitsberg et al. *European Journal of Biochemistry*, vol. 230, pp. 872–878, 1995.
Spitsberg et al. *Journal of Animal Science*, vol. 72, Supplement 1, abstract No. 286, 1994.
Spitsberg et al. *Journal of Animal Science*, vol. 72, Supplement 1, abstract No. 285, 1994.
Grosse, R. Et al, Mammary–Derived Growth Inhibitor, Springer–Verlag Berlin Heidelberg (1990) vol. 95 II.
Zavizion, I. Polittts et al, Effect of Mannary–Derived Growth Inbibitor on Proliferation of MAC–T Bovine Mammary Epithelial Cells, J. Dairy Sci (1993), 76:3721–3726.
Spitsberg, V.L. et al, Phosphorylation of Bovine and Human Milk Fat Globule Membrane (MFGM) and Bovine Skim Milk Membrane (SMM) Proteins: Effect of Metals, Inhibitors, and Troton X–100, The FASEB Jounal, Abstracats Part I, Mar. 9, 1995, vol. 9, No. 3.
Matitashvili, E. Et al, Effect of Mammary Derived Growth Inhibitor (MDGI/FABP), Isolated from Bovine Milk, on MAC–T and primary mammary epithelial cells: Comparison with a Synthetic MDGI/FABP Derivative, J. Anam Sci. vol. 77, Suppl. 1, (1994).
Spitsberg, V.T. et al, Predicting Production Responses of Cows Receiving bST using Milk Fat, Dairy Management, Inc., Research Funding Application, Jul. 1995.
Spitsberg, V.T. et al, Milk Fat Globule Membranes (MFGM) as a Source of Signal Transduction Pathway Components of Mammary Gland Spithelial Cells, ASBMB Meeting, May 1994.

*Primary Examiner*—Jill Warden
*Assistant Examiner*—Maureen M. Wallenhorst
*Attorney, Agent, or Firm*—Barnard, Brown & Michaels, P.C

[57] ABSTRACT

The invention relates to measuring the decrease in phosphorylation of the fatty acid binding protein (FABP) found in the milk fat globule membrane (MFGM) of bovine or human milk to detect growth hormone treatment in animals. MFGM of cows treated with recombinan+bovine somatotropin (bST) displays weaker FABP autophosphorylation activity than non treated cows. MFGM isolated from cows treated with bST have significantly reduced levels of phosphorylated FABP. The bST test of the present invention can be used not only to determine whether the animal producing the milk has been treated with bST, it can also be used to determine the efficacy of bST on milk production. Dairy managers could thus base their decision on whether to continue bST treatment on such a test.

7 Claims, 1 Drawing Sheet

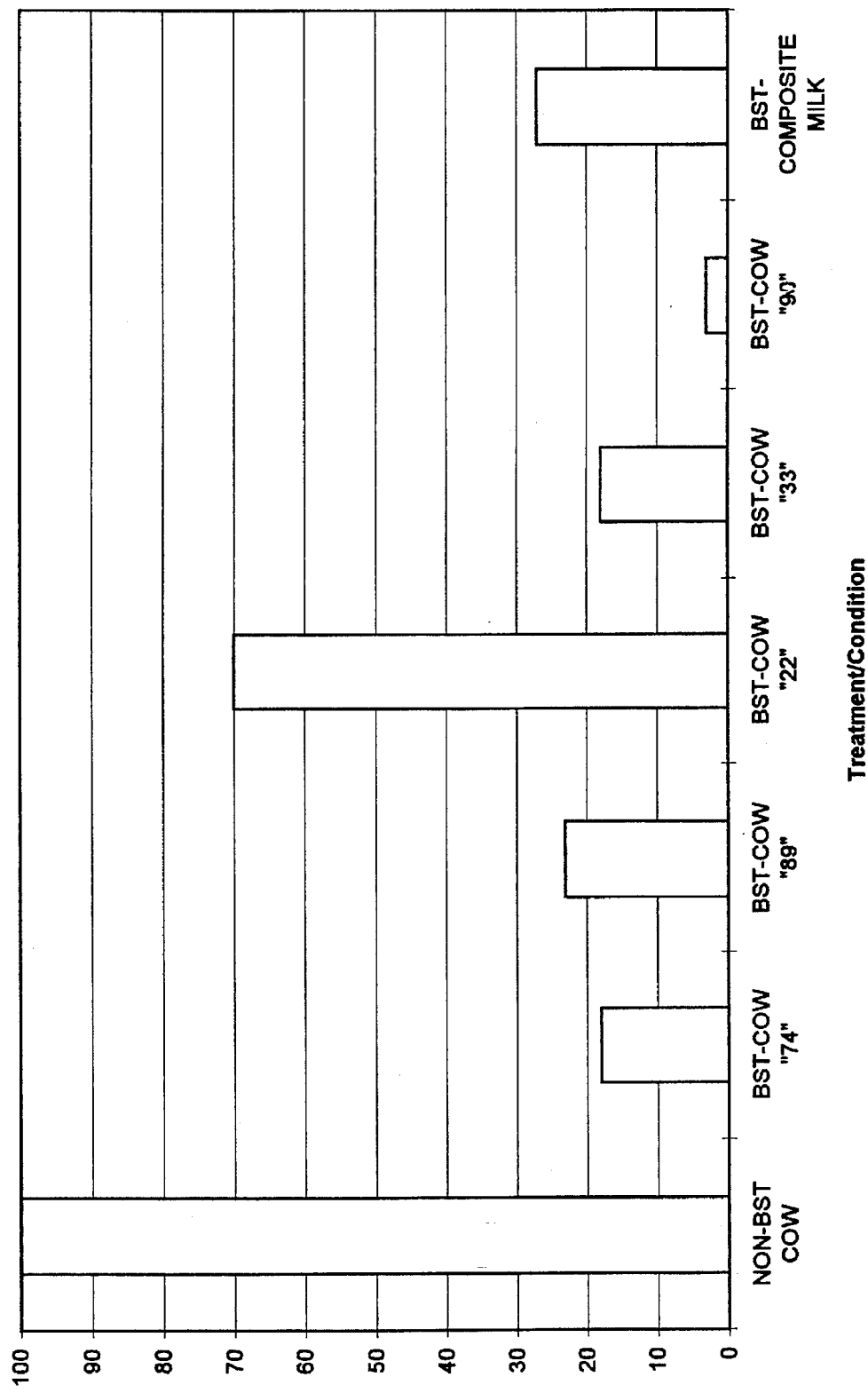

METHOD TO DETECT HORMONE TREATMENT IN ANIMALS

FEDERAL SPONSORED RESEARCH

The subject matter described herein was in part developed under USDA grant number 92-27206-779 of which the present inventors were the principal investigators and Cornell University was the Grantee.

FIELD OF THE INVENTION

The invention relates to a diagnostic test to detect a condition that affects a growth hormone in animals. Specifically the invention teaches measuring the decrease in phosphorylation of the fatty acid binding protein found in the milk fat globule membrane of bovine or human milk to detect growth hormone treatment.

BACKGROUND OF THE INVENTION

The United States Food and Drug Administration has approved the use of recombinant bovine somatotropin (bST) in dairy cows and the hormone has widespread use. The use of bST has sparked a nationwide controversy regarding economic, health and political issues. The controversy has led some dairy product distributors to mark their products with claims that the products are bST free or that the cows used to produce the milk were not treated with bST. However, currently there is no simple test for determining whether milk has come from an animal treated with the hormone.

In addition, there is presently no test to predict the production response of cows to bST treatment. Therefore, the dairy manager may be wasting resources administering bST to cows which are not responding to the hormone.

Milk Fat Globule Protein

One remarkable feature of milk is the presence of lipid droplets coated with proteo-lipid material, or, as it is usually referred to as the milk fat globule membrane (MFGM). The MFGM is composed of four layers: the thin membrane, possibly derived from intracellular lipovesicles; the protein coat; the lipid bilayer, primarily derived from the apical plasma membrane and possibly secretory vesicle membranes; and the glycocalyx. Milk protein synthesis during lactation is simultaneously accomplished by the intensive synthesis of membrane components needed to replenish their loss by their extrusion from mammary gland secretory cells. In this sense, milk is a unique deposit of biological membranes synthesized inside secretory epithelial cells.

The study of MFGM proteins has received much attention over the years. Many proteins of the MFGM have been well characterized. Some of the genes encoding these proteins have been cloned. Certain proteins of the MFGM are of special interest because of their involvement in important cellular processes. Milk fat globule membrane (MFGM) contains large quantities of the novel protein named mammary derived growth inhibitor [MDGI or FABP (fatty acid binding protein)] a 15 kDa protein. This milk fat derived MDGI/FABP inhibits the growth of various cell types, including bovine mammary and human breast cancer cells.

Fatty Acid Binding Protein FABP/MDGI

Several experiments have been conducted to illuminate the physiological mechanism whereby milk fat derived MDGI/FABP inhibits the growth of mammary cells. One of the experiments has proven that MDGI/FABP is in a phosphorylated form when it is present in mammary cells. The MDGI/FABP is phosphorylated on tyrosine. It is believed that the physiological activity of MDGI/FABP is regulated through its phosphorylation by protein kinases. Protein kinase activity exists in the milk fat globule membranes obtained from bovine and human milk.

Other experiments designed to determine the mechanism of MDGI/FABP on mammary cell growth and differentiation have led to the discovery that MDGI/FABP is in close association with the glycoprotein CD36 within the MFGM. CD36 is an abundant protein found in milk fat from cows. It is involved in cellular differentiation, lipid transport and sequestering oxidized fatty acids in milk. The information currently available suggests that the inhibitory action of MDGI/FABP and its synthetic analogs on cell proliferation is manifested through their interaction with the ectodomain of CD36. Moreover, CD36 may be a receptor for MDGI/FABP.

Relationship Between Fatty Acid Binding Protein (FABP/MDGI) and Bovine Somatotropin Bovine somatotropin treatment in dairy cows results in a net reduction in body fat accretion during the initial period of bST treatment so that nutrients can be diverted for milk synthesis. Lipid metabolism readjusts with chronic bST use, as voluntary feed intake increases. More specifically, the reduction in the ability of insulin to inhibit hepatic glucose synthesis and to stimulate glucose use by peripheral tissues represents a series of coordinated responses, whereby more glucose can be used for milk synthesis while preserving the ability of the animal to maintain glucose homeostasis. Similarly, adipose tissue response to acute signals that stimulate fat synthesis, such as insulin, is reduced, whereas the response to homeostatic signals that affect rates of fat mobilization is enhanced (stimulation by catecholamines, inhibition by insulin).

Most dairy managers have worked under the assumption that there is no physical difference in the milk obtained from cows treated with bST and those that are not supplemented with the hormone (as cows naturally produce bST). MFGM isolated from cow or human milk possesses intrinsic protein phosphorylation activity. Neither protein phosphorylation in MFGM nor the phosphorylation effect of bST on FABP had been previously studied.

SUMMARY OF THE INVENTION

The present invention includes the discovery that the MFGM of cows treated with bST displays weaker FABP autophosphorylation activity than non treated cows. MDGI/FABP is involved in the binding and transport of milk fatty acids. The teachings of the present invention demonstrate that the MFGM isolated from cows treated with bST have significantly reduced levels of phosphorylated FABP. The present invention includes a test for bST treatment by measuring the level of phosphorylated FABP.

The bST test of the present invention can be used not only to determine whether the animal producing the milk has been treated with bST, it can also be used to determine the efficacy of bST on milk production and to optimize bST production. Dairy managers could thus base their decision on whether to continue bST treatment on such a test.

Furthermore, this is the first time that a relationship between growth hormone and FABP phosphorylation has been described. By looking for variations from normal levels of FABP phosphorylation, conditions that affect growth hormone activity can be discovered.

BRIEF DESCRIPTION OF THE FIGURES

FIG. 1 is a bar graph showing intensity of a band on an electrophoresis gel showing FABP phosphorylation at the 15 kDalton level.

DETAILED DESCRIPTION OF THE PREFERRED EMBODIMENT

The present invention demonstrates for the first time that MFGM isolated from cow or human milk possesses different intrinsic protein phosphorylation activity for cows treated with bST and untreated cows.

The test for determining whether an animal has been treated with bST is performed by: 1) isolating the milk fat globule membranes (MFGM); 2) phosphorylating the MFGM; 3) and detecting the levels of phosphorylation of FABP in MFGM.

Isolation of Milk Fat Globule Membranes

Milk fat globule membranes (MFGM) are prepared from the cream of fresh bovine milk. Between 100–200 ml fresh bovine milk from cows administered bST are collected. The cream is obtained by centrifugation of milk at 3,000×g for 20 min. It is then suspended in two volumes of 10 mM phosphate buffer, pH 7.4, containing 0.9% NaCl (PBS), and homogenized in a Warring blender for 45 sec. The homogenate is centrifuged at 100,000×g for 90 min. The MFGM pellet is washed once by resuspension in an initial volume of PBS, followed by centrifugation at 100,000×g for 90 min. No cells (somatic cells) are found in the MFGM, as determined by light microscopy. MFGM may be either used immediately or stored at −80' C. for future use.

MFGM and skim milk membranes (SMM) were incubated with $\gamma\,^{32}$P-ATP in the presence of protein phosphatase inhibitors (vanadate, 8-glycerophosphate, phosphotyrosine, phosphoserine, phosphothreonine, p-nitrophenyl phosphate) and 5 mM MgCl, and/or 3 mM MnCl, led to phosphorylation of proteins, as detected by SDS-PAGE and autoradiography. In the bovine MFGM, 15 main radiolabelled protein bands were detected and ranged from 13–200 kDa (13, 15, 21, 24, 32, 35, 39, 45, 51, 66, 75, 100, 130, 200). In the human MFGM, 8 bands were indentified and ranged between 20–150 kDa five main bands corresponding to 51, 65, 66, 100, and 130, and three weaker bands corresponding to 21, 24 and 27 kDa. Phosphorylation of bovine skim milk membrane (SMM) proteins was observed only after the addition of 0.1% Triton X-100 to membranes. In this case, the three-four main radioactive bands were detected in a zone between 32 and 35 kDa, and one band in the 75 kDa range.

Auto-phosphorylation of MFGM

The presence of phosphatase inhibitors in the kinase media was necessary to see maximal levels of protein phosphorylation. The phosphorylation reaction would not take place when $Mg^{2+}$ and $Mn^{2+}$ were substituted for $Ca^{2+}$. Genistein, an inhibitor of protein tyrosine kinase activity caused approximately 50% inhibition of phosphorylation. Oubain, valinomycin with or without KCl, ionophore A23187+$CaCl_2$, atractyloside, dicyclohexylcarbodiimide (DCCD), carbonyl-cyanide-m-chlorophenyl hydrazone (CCCP) did not significantly alter the phosphorylation pattern.

It is believed that the observed phosphorylation was a result of $Mg^{2+}$ or $Mn^{2+}$—dependent protein kinase activity of the resident proteins present in the MFGM. The study showed that neither Ca-dependent ATPase, oubain sensitive -ATPase, or ATP/ADP- transporter stimulated or initiated kinase activity in MFGM proteins.

Relationship Between Phosphorylation and bST Treatment

FABP/MDGI is involved in the binding and transport of milk fatty acids. FABP of cows treated with bST displays weaker autophosphorylation activity than non treated cows. We have demonstrated that the MFGM isolated from cows treated with bST have significantly reduced levels of phosphorylated MDGI/FABP.

FIG. 1 is a bar graph showing intensity of a band on an electrophoresis gel showing FABP phosphorylation at the 15 kDalton level. The non-bST treated cow was used as a control. A sample from a milk bulk tank containing milk from cows treated with bST has only about a quarter of the phosphorylated 15 kDa protein. The individual cows varied more, but still showed a significant decrease.

The present invention includes a test for determining whether milk is from an animal treated with growth hormone. The first step is to establish a control providing a control reference for levels of phosphorylation of fatty acid binding protein from milk fat globule membranes from an animal that was known to be treated or not treated with growth hormone. The levels of phosphorylation of fatty acid binding protein in a milk sample and the control are compared. The last step is to indicate whether the detected level of phosphorylation matches the control reference. Preferably, the control reference is established from at least one animal that was not with growth hormone and the sample is identified as produced from an animal treated with growth hormone if the detected level of phosphorylation is less than 75% that of the control reference, more preferably less than 50% that of the control reference and most preferably, less than 30% that of the control reference.

This same test can be used to determine whether an animal has a condition that is affecting production or function of growth hormone. By comparing phosphorylation levels of fatty acid binding protein from a sample to a control reference, abnormal conditions can be detected.

It is known that some animals respond better than others to hormone treatment, however, there is no easy test to predict an animal's response or to optimize bST treatment. Too much or too little growth hormone can influence milk yield. The present invention also includes methods for predicting an animal's response to growth hormone treatment and for determining the optimum level of hormone treatment.

To determine the optimum level of hormone treatment a sample is taken from the animal to be tested. The level of phosphorylation of fatty acid binding protein is detected in the sample. A control reference for levels of phosphorylation of fatty acid binding protein from milk fat globule membranes from at least one animal that was known to be treated with an optimum level of growth hormone is generated. The detected level of phosphorylation is then compared to the control reference. Then the level of hormone treatment is increased or decreased in response to the comparison.

To determine whether a lactating animal is likely to respond favorably to growth hormone treatment a sample of milk is taken from an animal to be tested. The level of phosphorylation of fatty acid binding protein is detected in the sample. A control reference for levels of phosphorylation of fatty acid binding protein from milk fat globule membranes from at least one animal that was known to have responded favorably to growth hormone treatment. The detected level of phosphorylation is then compared to the control reference. Then the sample is marked whether the animal is likely to respond favorably to growth hormone treatment in response to the comparison.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of determining whether a lactating animal is being treated with a growth hormone comprising the steps of:
    a) providing a sample of milk from an animal to be tested;
    b) providing a control reference for levels of phosphorylation of fatty acid binding protein from milk fat globule membranes from at least one animal that was known to be treated or not with growth hormone;
    c) detecting levels of phosphorylation of fatty acid binding protein from milk fat globule membranes in said samples;
    d) comparing said detected level of phosphorylation to said control reference;
    e) indicating whether said detected level of phosphorylation matches the control reference whereby it is determined whether said animal is being treated with a growth hormone depending upon whether said detected level of phosphorylation in said sample matches that of said control reference.

2. The method of claim 1 wherein said control reference is established from at least one animal that was not treated with growth hormone and said sample is identified as produced from an animal treated with growth hormone if said detected level of phosphorylation is less than 75% that of the control reference.

3. The method of claim 1 wherein said control reference is established from at least one animal that was not treated with growth hormone and said sample is identified as produced from an animal treated with growth hormone if said detected level of phosphorylation is less than 50% that of the control reference.

4. The method of claim 1 wherein said control reference is established from at least one animal that was not treated with growth hormone and said sample is identified as produced from an animal treated with growth hormone if said detected level of phosphorylation is less than 30% that of the control reference.

5. A method of determining whether a lactating animal has a physiological condition which alters the physiologic or hormonal action of an administered growth hormone, comprising the steps of:
    a) providing a sample of milk from an animal to be tested;
    b) providing a control reference for levels of phosphorylation of fatty acid binding protein from milk fat globule membranes from at least one animal that was known to have or not have a physiological condition which alters the physiologic or hormonal action of an administered growth hormone;
    c) detecting levels of phosphorylation of fatty acid binding protein from milk fat globule membranes in said sample;
    d) comparing said detected level of phosphorylation to said control reference;
    e) indicating whether said detected level of phosphorylation matches the control reference whereby it is determined whether said animal has a physiological condition which alters the physiologic or hormonal action of an administered growth hormone depending upon whether said detected level of phosphorylation in said sample matches that of said control reference.

6. A method of determining the optimum level of hormone treatment for optimum milk yield for a lactating animal that is being treated with a growth hormone comprising the steps of:
    a) providing a sample of milk from an animal to be tested undergoing a level of hormone treatment;
    b) providing a control reference for levels of phosphorylation of fatty acid binding protein from milk fat globule membranes from at least one animal that was known to be treated with an optimum level of growth hormone;
    c) detecting levels of phosophorylation of fatty acid binding protein from milk fat globule membranes in said sample;
    d) comparing said detected level of phosphorylation to said control reference; and
    e) optimizing milk yield in the animal from whence the sample is derived by increasing or decreasing said level of hormone treatment in response to said comparison of step d), so as to match the level of phosphorylation detected in the control reference.

7. A method of determining whether a lactating animal is likely to respond favorably to growth hormone treatment comprising the steps of:
    a) providing a sample of milk from an animal to be tested;
    b) providing a control reference for levels of phosphorylation of fatty acid binding protein from milk fat globule membranes from at least one animal that was known to have responded favorably to subsequent growth hormone treatment;
    c) detecting levels of phosphorylation of fatty acid binding protein from milk fat globule membranes in said sample;
    d) comparing said detected level of phosphorylation to said control reference;
    e) indicating whether said sample is from an animal likely to respond favorably to growth hormone treatment in response to said comparison of step d) by determining if the detected level of phosphorylation in said sample matches the level of phosphorylation in the said control reference.

* * * * *

UNITED STATES PATENT AND TRADEMARK OFFICE
CERTIFICATE OF CORRECTION

PATENT NO. : 5,635,401
DATED : June 3, 1997
INVENTOR(S) : Vitaly L. Spitsberg, et al It is certified that error appears in the above-identified patent and that said Letters Patent is hereby corrected as shown below:

Column 1, line 7 — Change "USDA grant number 92-27206-7779" to --USDA grant number 92-37206-7779--

Signed and Sealed this

Ninth Day of December, 1997

*Attest:*

BRUCE LEHMAN

*Attesting Officer*     Commissioner of Patents and Trademarks